(12) United States Patent
Staebler et al.

(10) Patent No.: US 10,849,674 B2
(45) Date of Patent: Dec. 1, 2020

(54) INSTRUMENT AND SYSTEM FOR ABLATION

(71) Applicant: Erbe Elektromedizin GmbH, Tuebingen (DE)

(72) Inventors: Thomas Staebler, Tuebingen (DE); Charlotte Herrberg, Bodelshausen (DE); Achim Brodbeck, Metzingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 335 days.

(21) Appl. No.: 15/917,295

(22) Filed: Mar. 9, 2018

(65) Prior Publication Data
US 2019/0167335 A1 Jun. 6, 2019

(30) Foreign Application Priority Data
Mar. 10, 2017 (EP) .................... 17160265

(51) Int. Cl.
*A61B 18/04* (2006.01)
*A61B 18/14* (2006.01)
(Continued)

(52) U.S. Cl.
CPC ........ *A61B 18/042* (2013.01); *A61B 1/00087* (2013.01); *A61B 18/1492* (2013.01);
(Continued)

(58) Field of Classification Search
CPC .............. A61B 18/042; A61B 18/1492; A61B 1/00087; A61B 1/2736;
(Continued)

(56) References Cited

U.S. PATENT DOCUMENTS

| 4,730,936 A | 3/1988 | Thorjusen |
| 8,641,711 B2 | 2/2014 | Kelly et al. |

(Continued)

FOREIGN PATENT DOCUMENTS

| CN | 101243732 A | 8/2008 |
| CN | 104023462 A | 9/2014 |

(Continued)

OTHER PUBLICATIONS

European Search Report in corresponding European Application No. 17160265.9, dated Sep. 27, 2017, 6 pages.
Chinese First Office Action dated May 29, 2020, in corresponding Chinese Application No. 201810194292.5, with English translation (13 pages).

*Primary Examiner* — Jaymi E Della
*Assistant Examiner* — Rachel A. Vierra
(74) *Attorney, Agent, or Firm* — Fitch, Even, Tabin & Flannery LLP

(57) ABSTRACT

An instrument for large-area ablation of the mucosa including at least one first gas supply line and at least one second gas supply line whose distal ends are arranged to form an acute angle (α), so that the ends diverge distally. A free space between the distal ends of the gas supply lines allows the user to view the tissue region behind the distal end of the instrument. Due to the acute angle (α), electrodes arranged at least partially in the ends of the gas supply lines generate a wide plasma beam with which the mucosa ablation can be performed. The instrument can be guided precisely due to the view through the free space. A connecting element according to the invention is provided for attaching the ends of the gas supply lines.

18 Claims, 6 Drawing Sheets

(51) Int. Cl.
*A61B 1/00* (2006.01)
*A61B 18/00* (2006.01)
*A61B 17/00* (2006.01)
*A61B 1/273* (2006.01)

(52) U.S. Cl.
CPC ... *A61B 1/2736* (2013.01); *A61B 2017/00477* (2013.01); *A61B 2018/00166* (2013.01); *A61B 2018/00494* (2013.01); *A61B 2018/00577* (2013.01); *A61B 2018/00982* (2013.01); *A61B 2218/005* (2013.01)

(58) Field of Classification Search
CPC ........... A61B 2017/00477; A61B 2018/00166; A61B 2018/00494; A61B 2018/00577; A61B 2018/00982; A61B 2218/005
See application file for complete search history.

(56) References Cited

U.S. PATENT DOCUMENTS

| | | |
|---|---|---|
| 2003/0181900 A1 | 9/2003 | Long |
| 2005/0118350 A1 | 6/2005 | Koulik et al. |
| 2006/0184097 A1 | 8/2006 | Quinn |
| 2007/0029292 A1 | 2/2007 | Suslov et al. |
| 2010/0114092 A1* | 5/2010 | Eisele .................. A61B 18/042 606/41 |
| 2011/0184408 A1 | 7/2011 | Konesky et al. |
| 2014/0239812 A1 | 8/2014 | Valdes et al. |

FOREIGN PATENT DOCUMENTS

| | | |
|---|---|---|
| EP | 0346613 A1 | 12/1989 |
| WO | 2008090004 A1 | 7/2008 |
| WO | 2011022069 A2 | 2/2011 |

* cited by examiner

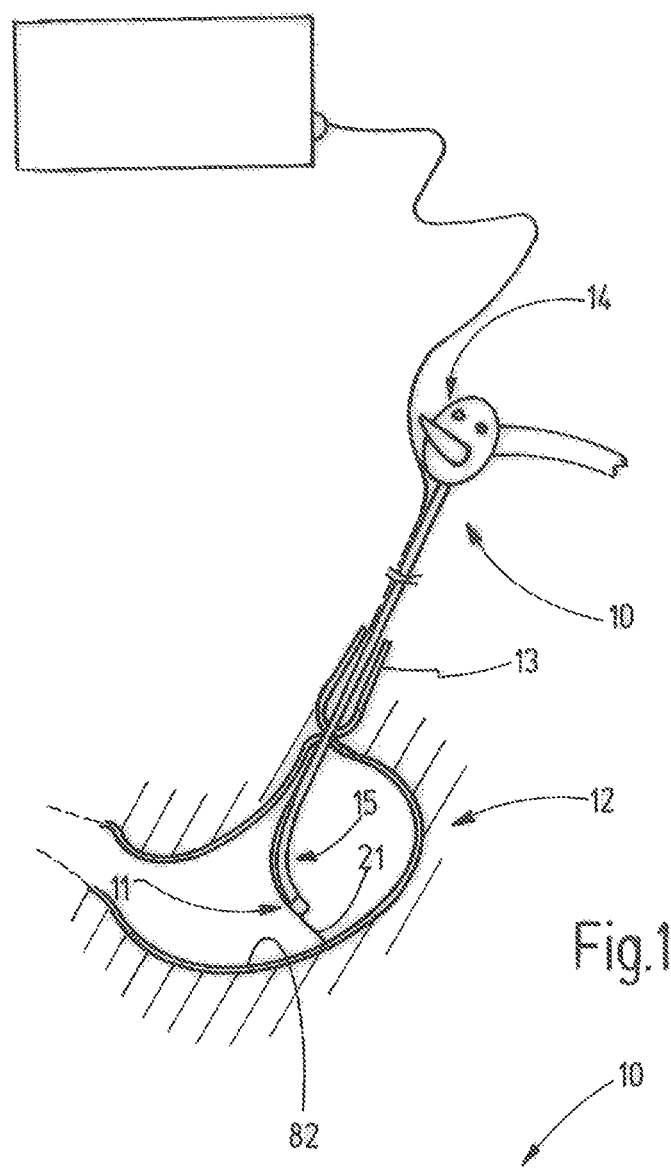
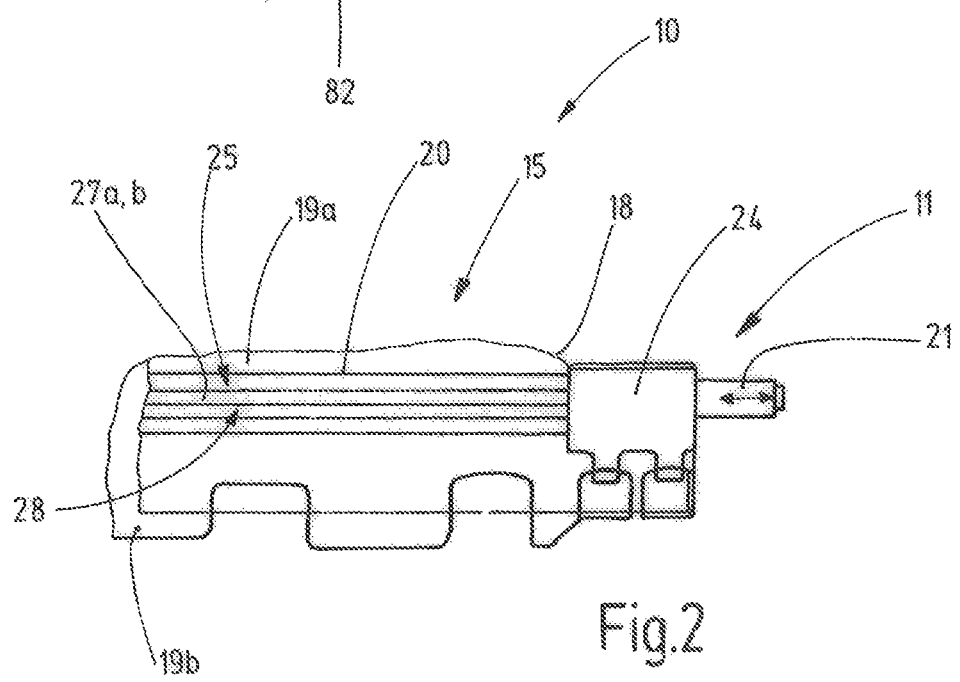
Fig.1
Fig.2

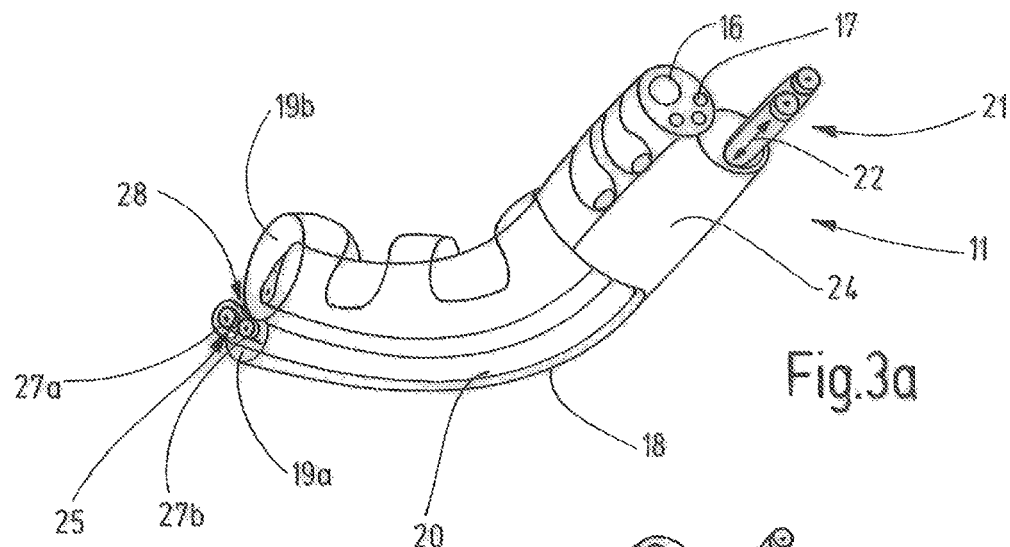
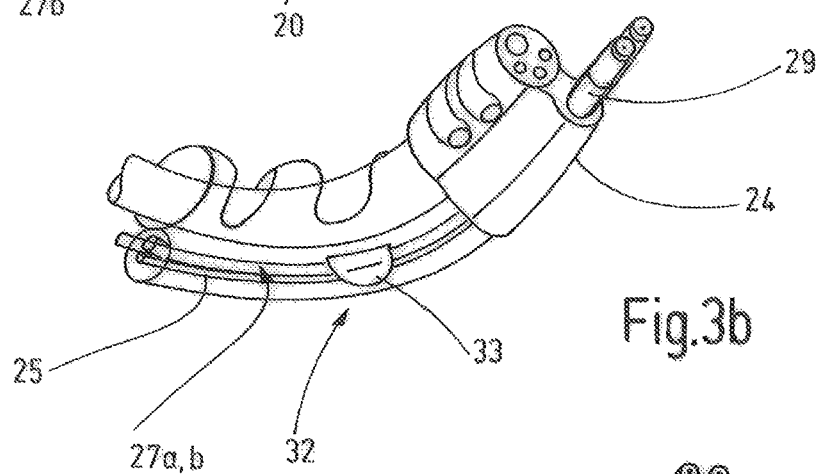
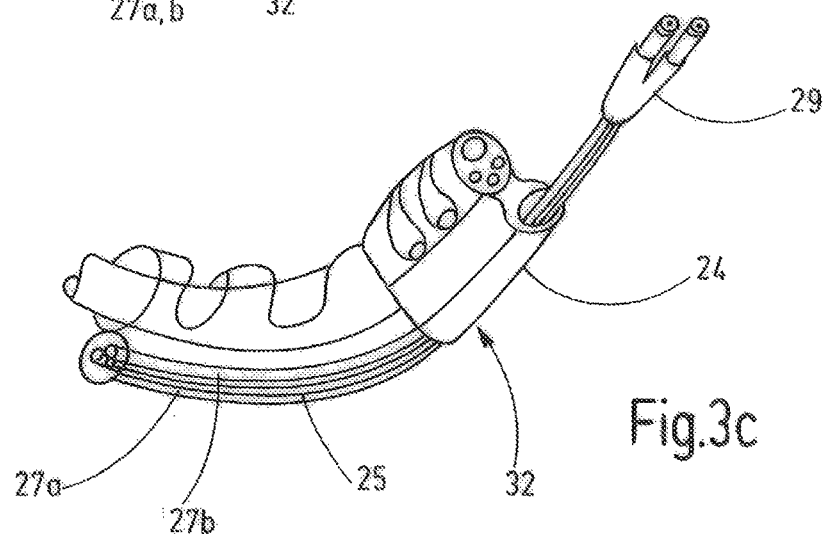
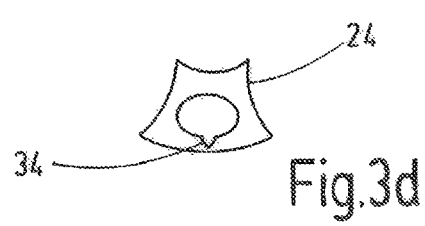
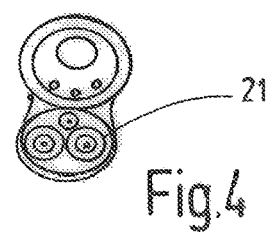

INSTRUMENT AND SYSTEM FOR ABLATION

RELATED APPLICATION(S)

This application claims the benefit of European Patent Application No. 17160265.9 filed Mar. 10, 2017, the contents of which are incorporated herein by reference as if fully rewritten here.

TECHNICAL FIELD

The invention relates to a device for ablation, in particular for mucosa ablation.

BACKGROUND

Publication WO 2008/090004 A1 describes a bipolar instrument with two channels for the treatment of tissue, each of said channels containing an electrode. The channels are disposed for supplying inert gas to the electrodes in order to produce an electric arc between the two electrodes.

The instrument for generating a plasma for electrosurgical treatment described in publication US 2011/0184408 A1 comprises two gas channels, each with an electrode, with the arrangement of which plasma discharges are to be generated, these being combined in front of the instrument.

Therapeutic mucosa ablation, for example for the ablation of tumors or for the destruction of cells of the stomach walls that advantageously affect eating behavior for the reduction of weight, is typically performed by endoscopic intervention, in which case special probes are being used.

Regarding this, publication WO 2011/022069 A2, for example, has disclosed an endoscope with an end cap which is to be placed on the mucosa and wherein an argon plasma coagulation is performed in the inside space of said endoscope. The cap is to limit the region of effect of the argon plasma coagulation and thus define the mucosa coagulation.

Publication U.S. Pat. No. 8,641,711 B2 discloses an instrument for the ablation of tissue layers of hollow organs, wherein the instrument comprises an electrically active head comprising electrodes, on which head an expandable element is provided for positioning the head of the instrument in a defined manner relative to the oppositely located tissue wall. This instrument assumes the existence of hollow organs with a confined diameter such as is the case, for example, with the intestine.

Large-area mucosa ablation poses particular challenges to the practitioner, in view of patience and dexterity. This is true, in particular, if flexible instruments provided for general use such as polypectomy loops or the like are used. With the use of such loops only one resection of the mucosa of approximately 2 cm$^2$ is performed in one working step. A resection between the gastric fundus and the cardia region of the stomach with the use of a flexible endoscope is very difficult. Furthermore, there is the risk of perforation.

Considering an ablation of the mucosa, both an inadequate ablation and too deep an effect should be rejected because underlying tissue layers could be damaged—up to and including the perforation of the stomach. Overall, a smooth and safe procedure during treatment is desirable. Furthermore, an undesirable thermal stress of the tissue during the entire procedure should be avoided.

SUMMARY

The object to be achieved with the invention may be achieved with the embodiments disclosed and claimed herein.

The instrument according to the invention is suitable for the large-area tissue treatment, preferably tissue ablation, for example mucosa ablation. The instrument according to the invention comprises at least one first gas supply line and one second gas supply line, wherein the gas supply lines are disposed for the supply of a gas, preferably an inert gas, in particular argon. A first electrode is arranged at least partially in the first gas supply line. A second electrode is arranged at least partially in the second gas supply line. The first gas supply line and the second gas supply line are arranged relative to each other in such a manner that the distal end of the first gas supply line forms an acute angle with the distal end of the second gas supply line, so that the distal ends of the gas supply lines diverge in different directions. Due to the acute angle, it is possible—when the gas supply lines are charged with gas—to generate a gas flow in the end of the first gas supply line and a gas flow in the end of the second gas supply line, in which case the directions of flow of both gas flows form the acute angle. Preferably, the angle is between a minimum of 1° and a maximum of 60°, particularly preferably between a minimum of 1° and a maximum of 30°, for example 10°. The first electrode and the second electrode may also form an acute angle, for example of the same size, so that the first electrode and the second electrode diverge in distal direction. The first gas supply line and the second gas supply line are arranged relative to each other in such a manner that a free space is provided between the distal end of the first gas supply line and the distal end of the second gas supply line. This free space allows a view between the ends of the gas supply lines through to the region of effect of the instrument in front of the distal ends of the gas supply lines.

When an RF voltage is applied to the electrodes, a plasma, for example an argon plasma, can be produced by means of sparks generated on the electrodes. The plasma can be used for a treatment of the tissue located in front of the electrodes. In particular, the procedure comprises cutting and/or coagulating. Due to the arrangement of the ends of the gas supply lines relative to each other at an acute angle and/or due to the arrangement of the electrodes relative to each other at an acute angle, it is possible to achieve that the plasma flows originating from both ends of the gas supply lines will diverge and cut and/or coagulate a wide, strip-shaped region of the mucosa when the instrument is moved along the mucosa. The plasma streams exiting from the two ends of the gas supply lines combined can form an approximately fan-shaped stream, i.e., a stream having a non-circular (oval or strip-like) cross-section. The discharge orifices of the two gas supply lines are preferably located on a line that is oriented transversely with respect to the direction of movement of the instrument. When the angle between the two ends of the gas supply lines and/or between the two electrodes, as well as the outflow rate of the gas from the gas supply lines, the gas quantity, as well as the application of power of to the two electrodes are suitably specified, it can be achieved that—across the width of the coagulated strip of mucosa—there results, i.e., within the therapeutic meaning, a more uniform depth of effect. In doing so, it is possible to achieve a uniform and large-area tissue treatment, in particular ablation.

The concept according to the invention paves the way to designing a particularly narrow, slim instrument end that may be hardly wider—or in the individual case also narrower—than the track of coagulated mucosa tissue produced by said instrument.

Because of the free space between the ends of the gas supply lines the user of the instrument is provided an improved view of the region of effect of the instrument in front of the distal ends of the gas supply lines and in front of the ends of the electrodes, respectively. During the plasma surgical treatment of tissue with the instrument obliquely relative to the longitudinal axis of the distal end of the instrument, the free space provides the user of the instrument preferably with the possibility of looking between the distal ends of the gas supply lines through the free space at the region of effect of the instrument.

Furthermore, the free space keeps the thermal capacity of the instrument on the distal end of the instrument relatively low. If the end of the instrument becomes hot due to the plasma treatment, a more rapid cooling of the end of the instrument can be achieved, so that the instrument can be removed within a relatively short time from the body of the patient, without the risk of injury to healthy tissue by a hot instrument end. Due to the material "missing" in the free space, there will be no adhesion due to hot material at that location.

The connecting element according to the invention for the instrument according to the invention has a seat for the first gas supply line and a seat for the second gas supply line. The seats are configured in such a manner that the gas supply lines can be arranged in the seats in such a manner that the distal ends of the gas supply lines form an acute angle as described, so that the gas supply lines diverge at their distal ends in distal direction. Preferably, the seats are configured in such a manner that they specify a certain size of the angle between the ends of the gas supply lines. Furthermore, the seats are disposed for the arrangement of the gas supply lines in the seats in such a manner that, between the distal end of the first gas supply line and the distal end of the second gas supply line, there is arranged the free space that allows a view between the ends of the gas supply lines to the tissue in front of the distal ends of the gas supply lines.

The seats of the connecting element may comprise means for the axial fixation of the gas supply lines in the connecting element. To do so, the seats may have form-fitting connecting means such as, for example, one or more abutments or means for the formation of a snap-lock connection and/or means for the formation of a frictional connection between the gas supply line and the connecting element. Preferably, the seats are disposed to specify a specific size of the distance of the ends of the gas supply lines with respect to each other and/or with respect to the distal end of the connecting element. Preferably, the connecting means are designed such that the connection between a gas supply line and the connecting element can be produced and/or released, while no connection and/or one connection is produced between the other gas supply line and the connecting element.

The free space between the distal ends of the gas supply lines is preferably distally open on both sides in a transverse direction in order to be able to look—from outside the instrument—between the ends of the gas supply lines through to the region of the tissue in front of the instrument. Alternatively or additionally, the free space preferably extends from the distal end of the first gas supply line to the distal end of the second gas supply line. Alternatively or additionally, the free space preferably widens in distal direction, between the gas supply lines. For example, the free space may widen distally at the acute angle that is formed by the distal end of the first gas supply line and the distal end of the second gas supply line.

Referring to the system according to the invention, the instrument according to the invention is attached to the outside of an endoscope. For example, the endoscope may comprise a working channel, wherein the instrument is preferably arranged outside the working channel. The instrument may be guided on the outside on the endoscope. As a result of this, it is possible, for example, to slide the instrument along the axis of the distal end of the endoscope. On the distal end of the endoscope, there may be provided a light source for illuminating the tissue in front of the instrument and/or an input for an image to be transmitted to a device on the proximal end of the endoscope (image guide). The instrument may be arranged on the endoscope in such a manner that the user can look, with the aid of the image guide, between the ends of the gas supply lines onto the tissue in front of the instrument.

The fact that the distal end of the instrument can be slid back and forth in axial direction, i.e., in longitudinal direction of the endoscope, facilitates handling—in particular during the ablation of tissue layers in large hollow organs such as, for example the ablation of the mucosa in the stomach. The distal end of the instrument may be moved out between 0 mm and 100 mm, in which case a moving-out distance of up to 50 mm is viewed as advantageous, and more than 30 mm of moving-out length are viewed as being optimal.

It is viewed to be particularly advantageous when a socket associated with the connecting element and mounted to the endoscope has a recess complementary to the non-round cross-section of the connecting element, into which the connecting element may move while retracting in proximal direction. In particular, the non-round cross-section may be provided on the distal end of the connecting element. The connecting element and the instrument end, respectively, are thereby restricted in their torsional flexibility in the socket. This considerably facilitates handling of the ablation instrument according to the invention. In particular, it can be ensured that the connecting element and the instrument end, respectively, are—due to the retraction—in a specific rotational position that can be maintained even after being moved out. The connecting element and the instrument element, respectively, can be brought into a desired position, preferably also in moved out state, e.g., by an elevation on the tube on the proximal end of the socket and a groove provided therefor.

The instrument according to the invention, the system according to the invention, as well as the method according to the invention, can be further developed displaying one or more of the features described herein.

The first gas supply line and the first electrode may belong to a first probe, and the second gas supply line and the second electrode may belong to another—second—probe, in which case the probes may be disposed to be used separately, independently of the respectively other probe, for plasma treatment. The first probe and the second probe can be held with the connecting element in such a manner that the distal end of the gas supply line of the first probe forms the acute angle with the distal end of the gas supply line of the second probe, so that the free space is located between the distal end of the first gas supply line and the distal end of the second gas supply line.

At least one of the probes is attached to the connecting element in the instrument, preferably in an interchangeable manner, or it can be mounted in the arrangement. In this way, the user can exchange one or more probes attached by means of the connecting element for a probe desired by the user.

In the inventive instrument, the ends of the gas supply lines may distally project beyond the connecting element. Consequently, the connecting element may be arranged—in the event of a treatment with the aid of the instrument—e.g., outside a region having a temperature that exceeds the temperature up to which the material of the connecting element is stable. The seats of the connecting element for the gas supply lines can be configured in such a manner that they fix the position of the gas supply line in the instrument relative to other gas supply lines. Accordingly, the seats can define a distal protrusion of the ends of the gas supply lines beyond the distal end of the connecting element. Preferably, the electrodes are arranged outside the connecting element. This can minimize the thermal stress of the connecting element. Due to this measure and/or an arrangement of the connecting element proximally set back in front of the end of the gas supply lines, said connecting element may be produced of a material that displays a relatively low thermal stress resilience. With the arrangement of the electrodes outside the connecting element, it is also possible to avoid leakage currents between the electrodes via the connecting element. Therefore, the danger of voltage flashovers is lessened.

Material that can be used for the connecting element may be, for example, ceramic, plastic material such as PEEK, PA or an elastomer such as silicone.

The first gas supply line preferably comprises a line of plastic material that extends, without interruption, proximally from in front of the connecting element through the connecting element up to distally behind the connecting element. Likewise, the second gas supply line comprises a line of plastic material that extends, without interruption, proximally from in front of the connecting element through the connecting element to distally behind the connecting element. If electrical lines for the RF supply of the electrode are guided in the gas supply lines, these electrodes are preferably electrically insulated in the lines of plastic material by the connecting element and/or preferably relative to each other Furthermore, the danger of leakages in the gas supply lines within the connecting element while gas undesirably leaks out are reduced when the gas supply lines are isolated from the connecting element, i.e., the gas supply lines are not formed in sections by the connecting element.

At least on their distal ends, the gas supply lines are preferably made of heat-resistant plastic material or ceramic. This allows the continuous operation of the ablation device, in particular for the ablation of larger regions of the mucosa.

Preferably, the first gas supply line has a ceramic tube on its distal end, and the second gas supply line has a ceramic tube on its distal end. The distal ends of the gas supply lines can thus be made in a heat-resistant manner. Furthermore, the ends of the gas supply lines being the ceramic tubes are particularly stiff.

The first gas supply line and/or the second gas supply line may comprise a ceramic tube on its distal end, for example, that is inserted in a plastic line, for example a flexible plastic tubing or plastic tubing in the gas supply line. The distal ends of the ceramic tubes may also project out of the plastic lines, so that the distal ends of the gas supply lines are formed by the ceramic tube. Due to the distal ends of the plastic lines arranged set back, accordingly, opposite the distal end of the ceramic tubes in proximal direction, the ends of the gas supply lines are particularly heat-resistant. The distal ends of the ceramic tubes project—on the ends of the gas supply lines—preferably distally beyond the distal ends of the plastic lines by an amount such that the thermal stress of the distal ends of the plastic lines does not exceed a specified degree of stress, for example a specific temperature, during the electrosurgical operation of the instrument. The distal end of the flexible plastic tubing or the plastic tube is preferably arranged outside a temperature zone on the distal end of the gas supply line at the edge of the temperature zone, in which case—in the temperature zone during electrosurgical operation of the instrument—there prevails a temperature that exceeds up to which the plastic line is stable.

Preferably, the plastic lines consist of a material with an anti-adhesive, preferably smooth, surface, e.g., PTFE, in order to avoid the adhesion of tissue. Regions of the ceramic tubes projecting beyond the distal ends of the plastic lines may have a finished surface or be provided with an anti-adhesive coating in order to avoid the adhesion of tissue.

The first and the second electrodes are preferably arranged and fastened in the ceramic tubes. The ends of the electrodes may distally project from the ceramic tubes or be arranged inside the ceramic tubes.

Preferably, the proximal ends of the ceramic tubes are arranged in the connecting element. This contributes to the stability of the arrangement of the ends of the gas supply lines. For example, the ceramic tubes can be inserted in the connecting element in order to clamp the walls of the plastic lines—at least on the distal end of the connecting element—between the ceramic tube and the connecting element, respectively, in order to axially fix the gas supply lines in the connecting element.

The instrument may comprise another probe, for example a fluid jet probe, in particular. This additional probe may be arranged relative to the arrangement of the first gas supply line and the second gas supply line up to at most one degree of freedom, fixed relative to the arrangement. The additional probe may be arranged in a seat of the connecting element for the additional probe. Preferably, the additional probe can be slid relative to the arrangement of the first gas supply line and the second gas supply line into and/or out of the free space in distal direction. For example, the additional instrument may be arranged in a slidable manner in a seat of the connecting element. Particularly preferably, the additional probe can be slid beyond the distal ends of the plasma treatment unit of the instrument. The distal end of the additional probe can thus be placed onto the tissue, without requiring that the distal ends of the gas supply channels and/or the electrodes be placed on the tissue. The distal end of the additional instrument can preferably be retracted in proximal direction behind the distal ends of the gas supply channels in order to allow a view of even more regions of the tissue between the ends of gas supply lines. Furthermore, the distal end of the additional probe in such a rest position is subject to less thermal less stress.

In order to facilitate handling of the instrument, the instrument may comprise a sliding element for guiding the instrument over the tissue. For example, the sliding element may be attached to the connecting element. The sliding element is arranged on the instrument according to the invention in such a manner that the sliding element—during the use of the instrument according to the invention—is located between the tissue and the instrument. The sliding element is arranged in such a manner that the instrument according to the invention—during use via the sliding element on the tissue—can lie proximally, for example, in front of the region of effect of the instrument. The distal ends of the plasma probes can thus be guided at a fixed distance from the tissue, for example a distance between 0-10 mm, preferably 0-5 mm, particularly preferably 0-3, over the tissue. The angle between the longitudinal axis of the distal instrument end and the tissue, in doing so, is preferably between 0° and 80°, particularly preferably between 20° and 30°.

Preferably, the instrument is a monopolar instrument. This means that, in this case, the neutral electrode is not provided on the instrument but attached in the form of a large-area patch to the patient. In doing so, the current does not discharge via the instrument but via the body of the patient into the neutral electrode.

The two electrodes on the distal end of the instrument are preferably electrically isolated relative to each other and connected to dedicated supply lines for supplying the electrodes with RF power. Preferably, the feed lines are passed through the gas supply lines.

With the use of the instrument according to the invention preferably pulsed RF power is applied to the two electrodes. Particularly preferably, with the use of the instrument according to the invention, electrical power is alternatingly applied to the electrodes, as a result of which a particularly uniform ablation effect and a uniform coagulation depth measured across the width of the produced ablation strip can be achieved. This is true, in particular, when high-frequency voltage within the range of several hundred Kilohertz is alternatingly applied to the two electrodes, in which case the change-over frequency (alternating frequency) between the two electrodes is a few Hertz. The power applied to the electrodes may range, for example between 10 Watts and 400 Watts, in particular between 80 Watts and 120 Watts.

With the use of the instrument according to the invention, it is possible to inject into the stomach wall a fluid, for example an NaCl solution—for example, with the fluid jet probe—before the thermal ablation of the mucosa in such a manner that a fluid cushion is formed under the desired ablation site. Subsequently, the orifice of the fluid jet probe may preferably be retracted in proximal direction behind the distal end of the arrangement of the plasma probes.

Additional details of advantageous embodiments of the invention are the subject matter of the description hereinafter, as well as of the drawings. They show in

BRIEF DESCRIPTION OF THE DRAWINGS

FIG. 1 a schematic representation of an instrument according to the invention in an endoscope, FIG. 2 a side view, partially in section, of a system according to the invention with an endoscope and, arranged thereon, an instrument for ablation according to the invention, FIGS. 3a, 3b, 3c a perspective view of the endoscope with the ablation instrument according to FIG. 2, FIG. 3d the socket for the instrument according to FIGS. 3a-c, in a view onto the proximal end of the socket, FIG. 4 a frontal view of the endoscope and the ablation instrument according to FIGS. 2 and 3, FIG. 5 a detail of a sectional view of an ablation instrument according to the invention, FIG. 6 a plan view of a detail of the ablation instrument according to the invention as in FIG. 5, FIG. 7 the electrical circuitry of the ablation instrument in the form of a circuit diagram, FIG. 8a an illustration of a view through the image guide of an endoscope onto an instrument according to the invention and onto the treatment region, FIG. 8b a schematic representation of the structure of a stomach wall, FIG. 9 a highly schematic representation of an instrument according to the invention on an endoscope, FIGS. 10a, b, c an exemplary embodiment of the instrument according to the invention.

DETAILED DESCRIPTION

Figure 5:
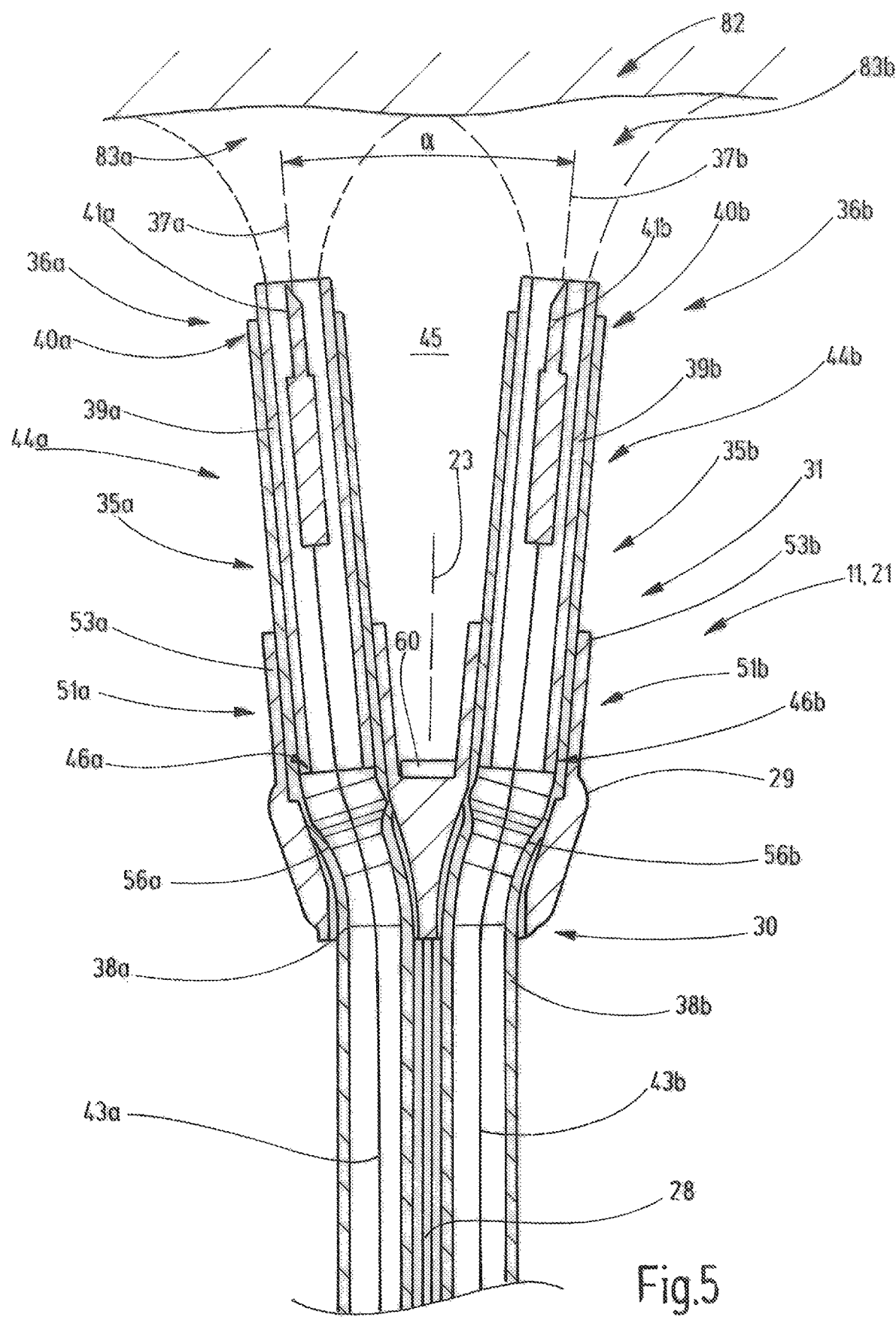

FIG. 1 illustrates the instrument 11 according to the invention attached to an endoscope 10 for ablation during the mucosa ablation procedure on a stomach 12. For treatment, the endoscope 10 and the instrument 11 are guided through the esophagus 13 into the inside space of the stomach 12. In doing so, control elements 14 allow moving the endoscope 10 in such a manner that, for example, a distal end 15 of the endoscope can be moved in a curved manner and/or along the inside wall of the stomach in a targeted manner, as a result of which various points of the inside wall of the stomach can be reached easily. The endoscope 10 may contain one or more channels 16 (see, for example, FIG. 3a) in which the working means such as, for example, surgical instruments can be inserted and/or via which gaseous and liquid fluids can be supplied or discharged. The endoscope 10 may comprise means for image transmission in order to be able to visually control the treatment.

FIGS. 2-4 show the distal end 15 of the endoscope with the instrument 11 attached thereto. The instrument 11 may be arranged together with the endoscope 10, in a tubular sleeve 18 that contains a first lumen 19a for the instrument 11 and a second lumen 19b for the endoscope 10. The first and/or the second lumen 19a,b can be provided with a slit as shown by FIGS. 2 and 3 in order to facilitate bending of the endoscope 10. The tubular sleeve 18 may consist of a thin plastic foil that encloses the endoscope 10 and the instrument extending through a sheathing tube 20 with appropriate play.

In the present exemplary example, the instrument 11 is preferably formed as an instrument 11 attached to the outside of the endoscope 10 and extending in longitudinal direction of said endoscope. Alternatively, the instrument 11 may also be arranged as an instrument 11 inside a channel 16 of the endoscope 10, for example. The instrument 11 has a distal instrument end 21 (instrument head) which is preferably supported so as to be movable, preferably in axial direction 22, said axial direction coinciding with the longitudinal direction of the distal end 15 of the endoscope 10. Preferably, the instrument end 21 may additionally be rotatable about the longitudinal axis 23 of the instrument end by, for example, +/−90°. The instrument end 21 can be associated with a socket 24 that is held by the endoscope 10. The socket 24 has a passage opening into which the instrument end 21 can be moved.

A sheathing tube 20 arranged in the second lumen 19b is axially fixed relative to the endoscope 10, for example on the socket 24. The sheathing tube 20 is preferably slit in a spiral-shaped manner on its distal end, e.g., along a length of approximately 200 mm. Preferably, at least two gas supply line tubes 27a,b for the supply of gas to the instrument 11 are arranged in the sheathing tube 20 that acts as the guide tube. Furthermore, preferably an elongated movement transmission element 25, for example a metal filament coil, is arranged in the sheathing tube 20, said coil being disposed for shifting and rotating the instrument head 21. For example, the instrument end 21 can be moved back and forth in axial direction 22 in that the movement transmission element 25 connected to the instrument head 21 is moved back and forth. In addition, a fluid supply line 28 to the instrument head 21 may be guided in the sheathing tube 20.

The instrument end 21 is shown in plan view in FIG. 4. The instrument end 21 comprises a connecting element 29, whose task will be explained further below and which may have a cross-section deviating from the circular form. In any event, the deviations of the cross-section of the passage opening of the socket 24 and the form of the connecting element 29 are such that the connecting element 29, when retracted, finds its way into the passage opening of the socket 24 and, in doing so, rotates into the desired angular position.

In order to accomplish this, the connecting element 29 may have a circular cross section on its proximal end 30. At this location, for example, a circular cone may be formed. The cross-section of the cone then gradually transitions—starting at the proximal end 30 in the direction of the distal end 31—into the form deviating from the circular form as is obvious from FIG. 4, in which case the outside surface of the connecting element 29 is preferably free of steps that are set at the orifice of the passage opening of the socket 24 and thus could impair a retraction of the connecting element 29.

This design contributes considerably to making handling of the instrument 11 easier. When the instrument end 21 or the connecting element 29 is moved out of the socket 24 associated with the connecting element 29 far enough, so that only the proximal end 30 of the connecting element 29 is still positioned in the socket 24 or that the connecting element 29 is completely pushed out of the socket 24, the end 21 of the instrument 11 can be rotated via a rotation of the movement transmission element 25 into various angular positions. However, when the end 21 of the instrument 11 is retracted, the connecting element 29 finds its way into the socket 24 that moves the connecting element 29, and thus the instrument end 21, into the specified angular position. The movement of the instrument end 21 and the connecting element 29, respectively, into the desired position illustrated in FIGS. 3 and 4 is thus given automatically due to a positive fit between the connecting element 29 and the socket 24. The forms of the connecting element 29 and of the socket 24 are adapted to each other in such a manner that the connecting element 29 is fixed in radial direction not only in its end position when it is retracted in the socked 24 but essentially retains this orientation until the connecting element 29 exits fully from the socket 24. As a result of this it is possible to slide the instrument end 21 in axial direction, and it still essentially maintains its orientation of rotation. The length of the axial shift, wherein the connecting element 29 and thus the end 21 of the instrument 11 essentially maintain their position in radial direction, is, for example, 15 mm, preferably 10 mm, particularly preferably 8 mm.

The connecting element 29 may consist of ceramic, for example, preferably however of plastic. As described in conjunction with FIG. 5, the connecting element 29 can be made in particular of a material that is not stable and/or not dimensionally stable in temperatures prevailing in the plasma range.

In order to ensure the orientation of the instrument end 21 in radial direction when the connecting element 29 has been moved in axial direction far enough that it exists from the socket 24, the arrangement comprising the movement transmission element 25 and the gas supply line tubes 27a,b can be made with an anti-twist device 32 according to FIGS. 3b and 3c. For the sake of clarity, FIGS. 3b and 3c do not show the sheathing tube 25 or the fluid supply line 28. To accomplish this, the anti-twist device 32 has a shaped catch in the form of a spring 33. FIG. 3d shows the socket 24 with a groove 34 provided in the socket 24 on a channel through which the gas supply lines 27a,b, as well as the movement transmission element 25 and the fluid supply line 28 can extend. The spring 33 immerses in the groove 34 and thus secures the desired position in the moved-out state of the instrument end 21. FIG. 3c shows the instrument head 21 in a position in which the instrument head 21 cannot be rotated due to the spring 33 in the groove 34.

The anti-twist device 32 can be embodied, for example, by plastic overmolding. The anti-twist device 32 may be configured in such a manner that it, together with the socket 24, forms and end stop that delimits the maximum length that the connecting element 29 or the instrument end 21 can be moved in axial direction. It is possible to arrange the anti-twist device 32 at a distance from the socket 24 on the sheathing tube 20 so that, as a result of this, the orientation of rotation of the connecting element 29, and thus the instrument 21, is ensured in any axial position. To accomplish this, it is necessary that—just before the connecting element 29 leaves the socket 24—the spring 33 come already in engagement, or at least partial engagement, with the groove 34.

It is also possible to arrange the anti-twist device 32 in such a manner that the connecting element 29 and the instrument end 21, respectively, are held freely movable in the direction of rotation between the instrument's two end regions. In the event of such an exemplary arrangement, a rotation fixation of the instrument end 21 is ensured until the connecting element 29 leaves the socket 24 and then, again, when the spring 33 enters the groove 34. With a total axial movement of the connecting element 29 and the instrument end 21, respectively, of 50 mm, for example, the range of the fixed direction of rotation of the instrument 21 may assume an end position of approximately 15 mm in the regions of their respective end positions. In between, the instrument end 21 may also be held so as to be freely movable at approximately 20 mm in radial direction.

A longitudinal section of an exemplary embodiment of the instrument 11 according to the invention is shown by FIG. 5. In doing so, this may be, for example an instrument 11 as shown by FIGS. 1 to 4. The instrument 11 according to the invention comprises a first gas supply line 35a and a second gas supply line 35b that are arranged relative to each other in such a manner that the distal ends 36a,b of the gas supply lines 35a,b together form an acute angle α, preferably between a minimum of 1° and a maximum of 60°, particularly preferably between a minimum of 1° and a maximum of 30°, particularly preferably 10°, so that the ends 36a,b of the gas supply lines 35a,b diverge in distal direction. To do so, the ends 36a,b of the gas supply lines 35a,b have differently oriented center axes 37a,b that are marked by a chain line in FIG. 5. The center axes 37a,b together form the aforementioned angle α. The ends 36a,b of the gas supply lines 35a,b may be arranged in such a manner that their center axes 37a,b are located in a common plane.

The ends 36a,b of the gas supply lines 35a,b may have a circular cross-section or also deviating cross-sections such as an oval cross-section, polygonal cross-sections or the like. The gas supply lines 35a,b preferably consist of a flexible tube and a tube of plastic material. The plastic lines 38a,b may be end sections of the gas supply line tubes 27a,b or be connected to these. In addition to the plastic lines 38a,b, the gas supply lines 35a,b may comprise ceramic tubes 39a,b, in which case respectively one ceramic tube 39a,b is inserted in the distal ends 40a,b of the plastic lines 38a,b. The gas supply lines 35a,b are disposed for supplying a gas, in particular an inert gas, for example argon, to the distal end 21 of the instrument 11. However, it is also possible to supply active gases, aerosols or the like, for which the gas supply lines 35a,b can be used in the same manner.

At least one first electrode 41a is arranged in the end 36a of the first gas supply line 36a, and at least one second electrode 41b is arranged in the end 36b of the second gas supply line 35b. In the illustrated exemplary embodiment, the electrodes 41a,b are arranged in the distal ends of the ceramic tubes that form the distal ends 35a,b of the gas supply lines 35,b in the exemplary embodiment. The electrodes 41a,b that, for example, consist of a heat-resistant metal such as tungsten are preferably fastened in the ceramic tube 39a,b. To do so, each of the electrodes 41a, for example may comprise resilient (not illustrated) sections that, due to the spring force, brace against the inside surface of the ceramic tube 39a,b, so that each of the electrodes 41a,b is held due to frictional locking in the ceramic tube 39a,b. The electrodes 41a,b are preferably arranged centered in the orifices of the gas supply lines 35a,b and/or are oriented in longitudinal direction with respect to the center axes 37a,b. For example, the electrodes 41a,b may have the shape of a rod, spatula, knife or needle. The tips of the electrodes 41a,b may be located inside the gas supply lines 35a,b, as indicated by FIG. 5, or they may project therefrom. The first electrode 41a and the second electrode 41b together may form an acute angle, preferably between a minimum of 1° and a maximum of 60°, particularly preferably between a minimum of 1° and a maximum of 30°, for example 10°, in such a manner that the first electrode and the second electrode diverge distally. The size of the angle between the electrodes 41a,b may correspond to the size of the angle α between the ends 36a,b of the gas supply lines 35,b. The distance between the distal tips of the electrodes 41a,b is preferably several millimeters (e.g., 3 mm to 12 mm), wherein a distance of 5 mm to 10 mm, in particular of 6.5 mm, is particularly advantageous in order to achieve a uniform, wide-strip tissue ablation with homogenous ablation depth. The diameter of the tips of the electrodes 41a,b is preferably in the range of 0.2 to 1 mm, wherein a diameter of 0.4 mm was selected in the present exemplary embodiment. This has been found to be advantageous because of the high field strengths occurring due to the small diameter and hence both the good ignitability of the electrodes 41a,b and the resultant tissue effects.

The electrodes 41a,b are preferably isolated from each other. Electrical lines 43a,b extend through the gas supply lines 35a,b for supplying the electrodes 41a,b with RF power. The plastic lines 38a,b isolate the electrical lines 43a,b from other electrical lines 43a,b. The gas supply lines 35a,b with the electrodes 41a,b form plasma probes 44a,b for the electrosurgical treatment of tissue in front of the instrument 11.

Preferably, the ceramic tubes 39a,b project distally beyond the ends 40a,b of the plastic lines 38a,b. In this manner, the ends 36a,b of the gas supply lines 35a,b are made of ceramic and thus are particularly temperature-stable, even during continuous operation of the instrument 11 for large-area ablation. Furthermore, this may lengthen a leakage distance between the electrodes 41a,b, which improves the dielectric strength of the arrangement. Furthermore, the dielectric breakdown density between the electrodes 41a,b can be increased.

As an alternative to the arrangement shown by FIG. 5, the plastic line 39a,b and—if present—also the ceramic tube 39a,b may end, or end together, at the distal end 36a,b of the gas supply line. In particular if no ceramic tubes 39a,b are inserted in the ends 40a,b of the plastic lines 38a,b, the plastic lines 38a,b, or at least their distal ends 40a,b, consist preferably of heat-resistant plastic material.

Between the ends 36a,b of the gas supply lines 35a,b that are spread at the angle α, there is provided a free space 45 to form a spread, fork-shaped instrument head 21. The free space 45 that widens in distal direction extends transversely to the direction distal or proximal from the distal end 36a of the first gas supply line 35a up to the distal end 36b of the second gas supply line 35b. The free space 45 extends between the gas supply lines 35a,b from the distal ends 36a,b of the gas supply lines 35a,b proximally up to between the proximal ends 46a,b of the ceramic tubes 39a,b. In the exemplary embodiment shown by FIG. 5, the free space 45 furthermore extends between the gas supply lines 35a,b from the free distal end section of the ceramic tube 39a of the first gas supply line 35a up to the free distal end section of the ceramic tube 39b of the second gas supply line 35b. Furthermore, the free space 45 extends between the gas supply lines 35a,b from the section of the plastic line 38a of the first gas supply line 35a that distally projects from the connecting element 29 up to the section of the plastic line 38b of the second gas supply line 35a that distally projects from the connecting element 29.

Due to the free space 45 the instrument 11 offers the user of the instrument 11 a view between the ends 36a,b of the gas supply lines 35a,b through to the ablation site of the plasma probes 44a,b, in particular during the plasma treatment of the tissue with the instrument 11. In particular, the user can look from outside of the instrument 11—for example, with the aid of a means for image transmission on or in the endoscope 10 on which the instrument is arranged—between the tips of the plasma probes 44a,b through the free space 45 onto the tissue region 47 (see also FIG. 8a) behind the instrument 11 and/or record an image of the tissue region 47 behind the instrument 11. Inasmuch as the user can have a better view of the region of effect of the instrument 11 due to the free space 45, he/she is able to guide the instrument particularly smoothly and still safely. In addition, the instrument head 21—due to the free space 45—has a relatively low thermal capacity at the distal end which can become hot during use of the plasma probes 44a,b. As a result of this, the instrument 11 can again be quickly removed from the body of the patient after use. Undesirable tissue adhesions at the end of the instrument may be reduced due to the free space 45.

The instrument 11 shown by FIG. 5 comprises—for the arrangement of the distal ends 36a,b of the gas supply lines 35a,b relative to each other in such a manner that they form the angle α—a connecting element 29 with seats 51a,b for the gas supply lines 35a,b, said seats being disposed to fix the ends 36a,b of the gas supply lines 35a,b in the angle α relative to each other. The seats 51a,b preferably specify the angle α between the ends 36a,b of the gas supply lines 35a,b in order to facilitate the arrangement of the ends 36a,b of the gas supply lines 35a,b relative to each other during the assembly of the instrument 11.

In order to fix the ends 36a,b of the gas supply lines 35a,b in such a manner that they are at a fixed distance from each other, the seats 51a,b of the connecting element have fastening means for the axial fixation of the ends 36a,b of the gas supply lines 35a,b. The fastening means may be means for producing a positive-locking connection and/or means for the formation of a friction-type connection between the gas supply lines 35a,b and the connecting element 29. The gas supply lines 35a,b may be clamped in the connecting element 29. Alternatively or additionally, the connecting element 29 may have snap-lock connecting means that interact with corresponding means on the gas supply lines 35a,b. In the exemplary embodiment shown by FIG. 5 the gas supply lines 35a,b are axially fixed in the connecting element 29 by means of friction locking due to an oversize of the gas supply lines 35a,b.

The seats 51a,b can specify the distances of the ends 36a,b of the gas supply lines 35a,b from each other and/or from the connecting elements 29 in order to facilitate the arrangement of the ends 36a,b of the gas supply lines 35a,b during the assembly of the instrument 11. For fixing the distance, it is possible, for example, to provide stops or other positive-locking elements on the connecting element 29 and the gas supply lines 35a,b.

Due to the connecting element 29, it is possible to implement a modular construction of the instrument 11. For example, different probes 44a,b, in particular those for plasma coagulation, for example different designs, can be arranged relative to each other. With the connecting element 29, individual probes 44a,b, each being usable separately from the instrument 11, can be arranged in particular outside the seat 51a,b in the connecting element 29 (individual probes) relative to the instrument 11. As a result of this, distal ends of the individual probes 44a,b are arranged preferably at a fixed distance from each other at the acute angle α that is preferably specified by the seats 51a,b of the connecting element. Preferably, one or both plasma probes 44a,b can be interchanged, without destruction of the connecting element 29 and/or without requiring the disassembly of the plasma probe 44a,b that is to be interchanged. The plasma probes 44,b connected to the connecting element can preferably be removed from the respective connecting element 29 in order to replace them with another plasma probe 44a,b in the instrument 11. The functionality of the plasma probe 44a,b is preferably maintained when the probe is removed.

The connecting element 29 shown by FIG. 5 preferably tapers in proximal direction. As a result of this, a particularly slim design of the connecting element and thus the instrument head 21 is obtained.

The free space 45 between the distal ends 36a,b of the gas supply lines 35a,b preferably extends proximally at least up to the distal end 31 of the connecting element. The connecting element 29 shown by FIG. 5 comprises, on its distal end 31, two extensions 53a,b that are spread at an angle α and that may have the form of a tube or tubing, in which case the gas supply lines 35a,b extend through the extensions 53a,b. The extensions 53a,b form channels that are separate from each other in the connecting element 29, through which the gas supply lines 35a,b for the arrangement of the ends 36a,b of the gas supply lines 35a,b in the angle α and, preferably, for the axial fixation by means of a friction-type connection. The center axes of the straight extensions 53a,b together form the angle α and thus define the angle α between the ends 36a,b of the gas supply lines 35a,b. The free space 45 extends between the distal ends 36a,b of the gas supply lines 35a,b in proximal direction between the extensions 53a,b, so that the user can look onto the tissue between the extensions through the free space 45 between one extension 53a and the other extension 53b.

In the exemplary embodiment shown by FIG. 5 the proximal ends 46a,b of the ceramic tubes 39a,b are inserted in the extensions 53a,b of the connecting element 29. For the axial fixation of the ends 36a,b of the gas supply lines 35a,b by means of the connecting element 29, their plastic line wall is clamped between the ceramic tube 39a,b and the connecting element 29. The inside and the outside diameters of the plastic lines 38a,b can be expanded relative to a section in front of the distal end 40a,b of the plastic line 38a,b in order to receive the ceramic tube 39a,b. The expansion can be formed by pressing the ceramic tube 39a,b into the end 40a,b of the plastic line 38a,b. The straight ceramic tubes 39a,b extending from the distal end 36a,b of the gas supply lines 35a,b up to the connecting element 29 contribute to a stabilized gas flow through the ends 36a,b of the gas supply lines 35a,b. The gas flow cross-section in the ceramic tube 39a,b and the gas flow cross-section of the plastic line 38a,b are preferably the same proximally in front of the expansion.

As shown by FIG. 5, the plastic lines 38a,b may extend approximately parallel to each other at the proximal end of the connecting element 29 in front of the connecting element 29. As shown by FIG. 5, the gas supply lines 35a,b are arranged preferably at a distance from each other in the connecting element 29 transverse to the longitudinal extension of the gas supply lines 35a,b. As is also shown by FIG. 5, the gas supply lines 35a,b are arranged in the connecting element 29 preferably in such a manner that the sections 56a,b of the gas supply lines 35a,b in the exemplary embodiment of the plastic lines 38a,b form an angle within the connecting element 29 in front of the distal ends 35a,b of the gas supply lines 35a,b, said angle being greater than the angle α between the ends 36a,b of the gas supply lines 35a,b in order to provide a distance of the ends 36a,b of the gas supply lines 35a,b from each other and thus a width of the free space 45—independent of the angle α between the ends 36a,b of the gas supply lines 35a,b. Accordingly, gas supply lines 35a,b diverge in a section in the connecting element 29 in front of the distal end 36a,b of the gas supply lines 35a,b in distal direction—initially more than less. This results in a slim arrangement of the gas supply lines 35a,b in front of the sections. Furthermore, due to this, space for a head 60 of an additional probe, e.g., a fluid jet probe 61, can be created. The head 60 of the additional probe and the fluid supply line 28 are not shown as a sectional representation by FIG. 5.

As illustrated, the plastic lines 38a,b preferably extend without interruption through the connecting element 29. The plastic lines 38a,b isolate the electrical lines 43a,b from the respective connecting element 29.

The ends 36a,b of the gas supply lines 35a,b project distally beyond the distal end 31 of the connecting element 29—in the illustrated exemplary embodiment beyond the extensions 53a,b. Consequently, the connecting element 29 that is arranged set back proximally with respect to the distal ends of the plasma probes 44a,b, is at a distance from the zone at the distal ends 36a,b of the gas supply lines 35a,b at increased temperature. Therefore, the connecting element 29 can be made of a material that does not withstand temperatures prevailing in the zone for the plasma treatment.

Material that can be used for the connecting element 29 is, for example, a plastic material such as PEEK, PA or an elastomer such as, for example, silicone.

The electrodes 41a,b, as illustrated are preferably arranged outside the connecting element 29 at a distance from the distal end 31 of the connecting element 29. Leakage distances between the electrodes 41a,b via the connecting element 29 are thus particularly long.

Figure 6:
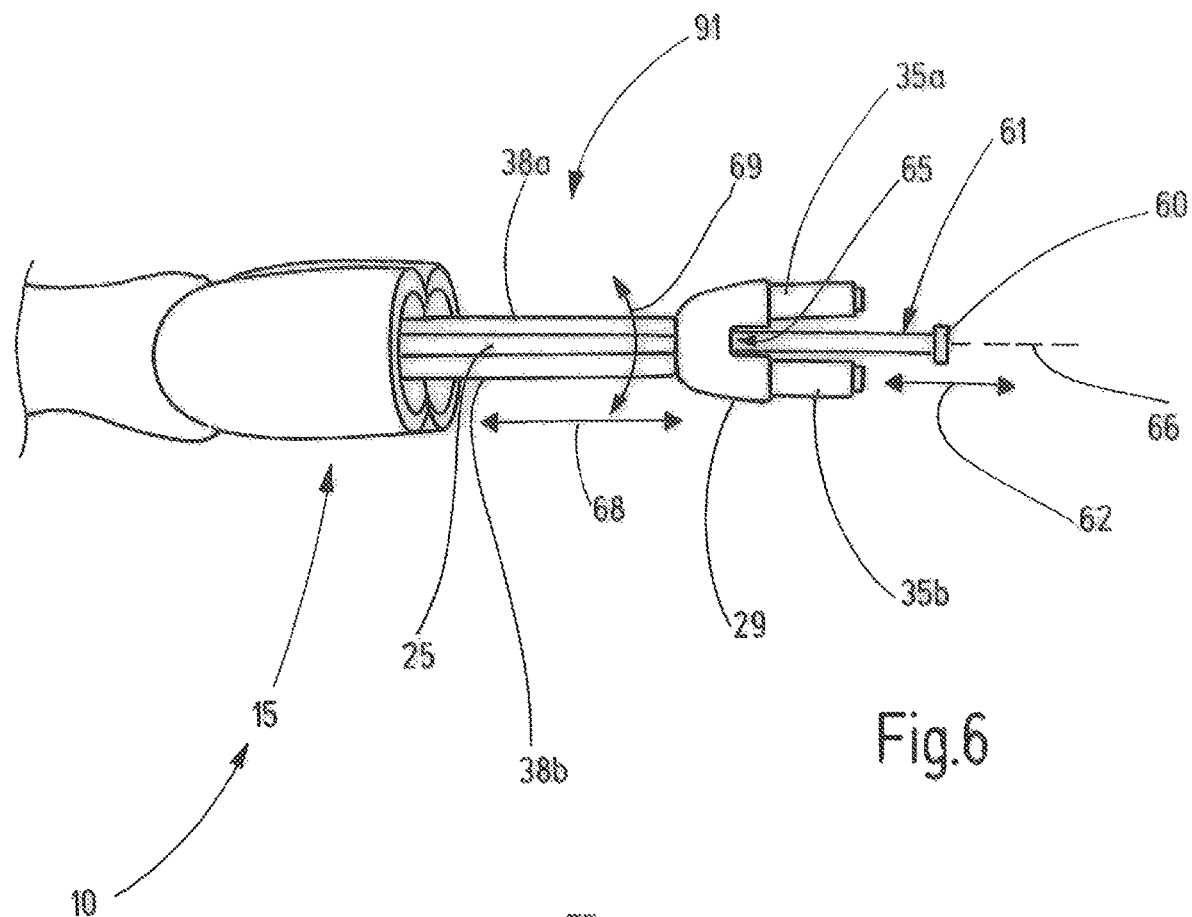

The mentioned additional probe 61, which the instrument 11 may comprise in addition to the plasma probes 44a,b, is shown by FIG. 5 in a rest position and in FIG. 6 in a working position slid beyond the distal ends of the plasma probes 44a,b. The slidability of the additional probe 61 is indicated by the double arrow 62. The additional probe 61 may be, for example, a fluid jet probe for the application of aqueous NaCl solution under the mucosa in order to lift the mucosa. With this probe, it is possible to generate a fluid jet at a pressure or flow required for injection under the mucosa, for example. To this extent, the fluid jet probe 61 comprises on its head 60 on the distal end of the fluid jet probe a nozzle with a discharge orifice through which a fluid, for example sodium chloride solution, can be ejected as a jet, for example. In doing so, it is possible to treat tissue regions, for example by subcutaneous injection, when the jet is ejected with appropriate pressure, flow and form so that it can penetrate the tissue like a needle. Preferably, the additional probe is held in a seat 65 of the connecting element 29 that is separate from the seats of the gas supply lines. As mentioned, the additional probe 61 is guided in the seat 65 in distal direction or proximally relative to the connecting element 29, preferably in a sliding manner. Alternatively thereto, the additional probe 61 may be fixed in the seat 65 relative to the connecting element 29, so that a movement of the head 60 of the additional probe 61 relative to the connecting element 29 is not possible.

The additional probe 61 is preferably guided in a sliding manner in distal direction so that the center axis 66 of the additional probe 61 is located above an imaginary line that connects the midpoints of the orifices of the gas supply lines 35a,b. The center axis of the sliding seat 65 in the connecting element 29 for the additional probe 61 is preferably arranged above an imaginary line oriented transversely with respect to the guiding direction from the center axis of the seat 51a for the first gas supply line 35a to the center axis of the seat 51b for the second gas supply line 35b. This is also the case in the exemplary embodiment illustrated by FIG. 5 and FIG. 6 that show the instrument from the bottom.

Due to the slidability of the additional probe 61 along the longitudinal axis 23 of the end of the instrument relative to the connecting element 29 and relative to the distal ends of the plasma probes 44a,b, respectively, the head 60 of the additional probe 61 can be slid in the distal direction relative to the arrangement of the ends 36a,b of the gas supply lines 35a,b into the mentioned working position, and the head 60 of the additional probe 61 can be moved relative to the arrangement in the direction proximal to the mentioned rest position.

Preferably, the additional probe 61 is arranged in such a manner that the head 60 of the additional probe 61 can be slid distally through the free space 45 arranged between the ends 36a,b of the gas supply lines 35a,b, beyond the distal ends of the plasma probes 44a,b into the working position, and that the head 60 of the additional probe 61 can be moved back through the free space 45 into its rest position proximal in front of the free space 45.

As shown by FIGS. 5 and 6, the additional probe 61 may have arranged on it a stop element, e.g., as formed by a head 60 that is widened relative to the fluid supply line—e.g., as in FIGS. 5 and 6—so that a further retraction of the head 60 of the additional probe in proximal direction beyond the rest position is prevented.

When the head 60 of the fluid jet probe 61 is slid distally beyond the ends of the plasma probes 44a,b, the head 60 of the fluid jet probe 61 can be placed on the tissue in order to inject NaCl solution into the tissue through the nozzle in the head 60, without—at the same time—having the distal ends of the plasma probes 44a,b in contact with the tissue. When the head 60 of the additional probe 61 is retracted into the rest position proximally in front of the free space 45, the user is provided an even more improved view onto the ablation site.

A cleaning element (not illustrated) can be arranged on the additional probe 61, with which cleaning instrument it is possible to slough off tissue adhesions or other contaminants on the plasma probes 44a,b.

Furthermore, FIG. 6 shows an example of an elongated movement transmission element that displays tensile stiffness, compression stiffness and torsional stiffness that, however, is easily bendable, and that allows a sliding (arrow 68) of the instrument head 21 back and forth relative to the distal end 15 of the endoscope 10, as well as a rotation (arrow 69) about an axis along the instrument 11. The movement transmission element is connected to the connecting element 29 and a control element 14 for transmitting the movement (see FIG. 1). The movement transmission element may be, for example, a preferably electrically isolated metal coil.

Figure 7:
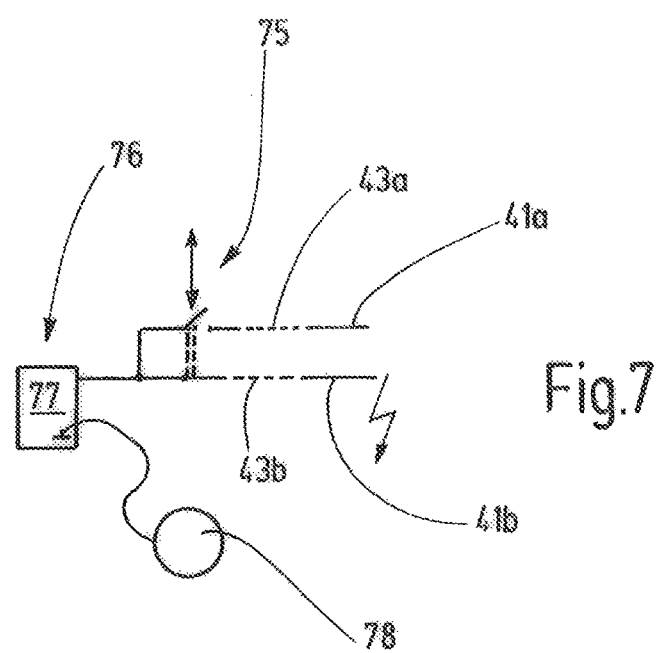

As illustrated by FIG. 7, the electrical lines 43a,b for the supply of the electrodes 41a,b with RF power are connected via a switch arrangement 75 to an electrical source 76, for example in the form of a high-frequency generator 77. It provides an RF voltage of several hundred Kilohertz (for example, 350 kHz) and a suitable voltage above 1000 Vp (e.g., between a minimum of 4 kVp and a maximum of 6 kVp, preferably 4.3 kVp or 4.9 kVp). The high-frequency generator 77 can generate an output of more than 100 Watts (for example, 120 Watts).

The voltage is provided with reference to a zero potential to which the patient is connected via at least one neutral electrode 78. This neutral electrode 78 is applied in a large area to a suitable location of the body of the patient. The switch arrangement 75 alternately connects the lines 43a,b and thus the electrodes 41a,b, i.e., alternating with the output of the high-frequency generator 77. The switching frequency with which the electrodes 41a,b are alternatingly activated is in the range of a few Hz, preferably between 1 Hz and 20 Hz, preferably 5 Hz.

The gas supply lines 36a,b for the plasma treatment can be charged with a combined gas flow of between, for example, a minimum of 1 Liter/minute to a maximum of 4 Liters/minute, preferably 2 Liters/minute.

Figure 8A:
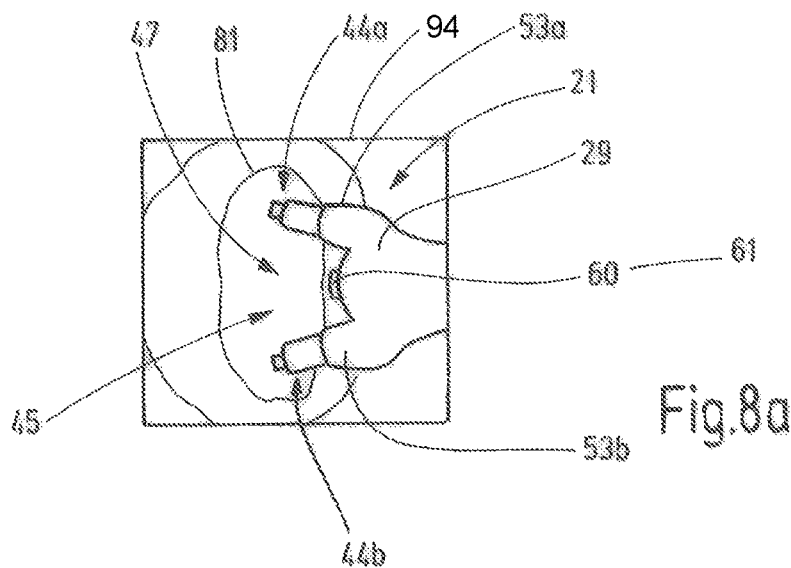

FIG. 8a shows an image 94 that is recorded with the aid of the means for image transmission in the endoscope 10. The instrument head 21 with the connecting element 29 and the ends of the plasma probes 44a,b and, furthermore, the tissue region 47 illuminated by the illuminating means on the endoscope can be seen through the endoscope 10. In the tissue region 47 there is a tissue site 81 that is to be treated with the instrument 11. The head 60 of the fluid jet probe 61 is retracted proximally out of the free space 45 into a rest position. As can be seen, the instrument head 21 that is spread in a fork-like manner offers, due to the view through the free space 45 between the ends of the plasma probes 44a,b and the extensions 53a,b, a clear view onto the tissue site 81. This considerably facilitates a safe and smooth guiding of the instrument 11.

The instrument 11 for ablation described so far works as follows: For the surface ablation of mucosa, for example for the therapeutic treatment of pathological tissue changes, for affecting the weight and eating behavior of patients or for other therapeutic reasons, the endoscope 10 provided with an instrument 11 for ablation according to FIG. 1 is inserted through the esophagus 13 of the patient into the patient's stomach 12. By means of the control elements 14 of the endoscope 10, the distal end 15 of said endoscope is positioned on the desired ablation site in such a manner that the tissue region to be treated is in the field of view of the endoscope 10. Now, by appropriate sliding of the arrangement out of the sheathing tube and the gas supply line tubes 13 and/or the movement transmission element 57, the distal end 21 of the ablation instrument 11 is slightly moved forward so that it is at the desired distance from the mucosa 84, for example 3 mm.

Figure 8B:
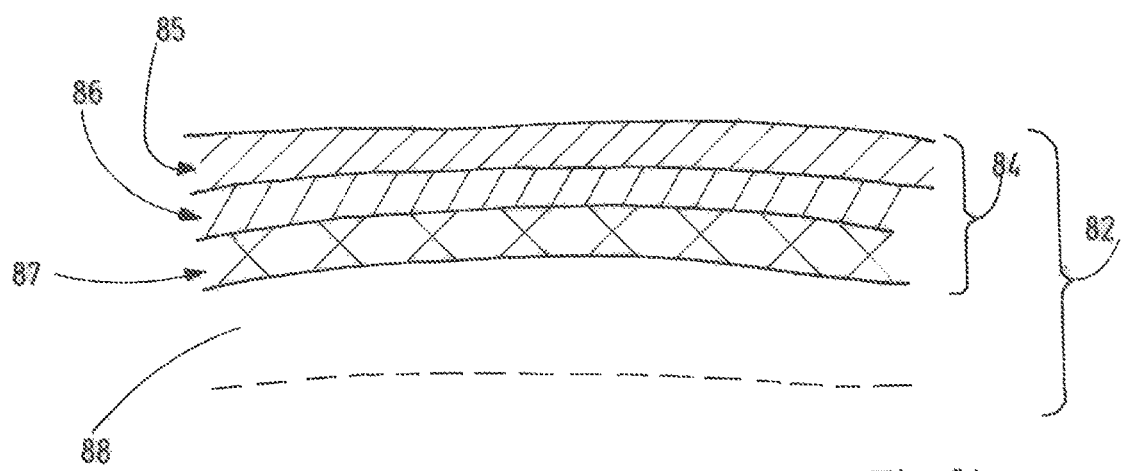

Prior to the thermal ablation of, for example, the mucosa 84 (see also FIG. 8b), fluid is injected into the stomach wall 82 via the discharge orifice on the head of the fluid jet probe 61, so that a fluid cushion is advantageously formed under the desired ablation site 81. Gas, for example argon, flows through the gas supply lines 35a,b. Now, the generator 77 and the switch arrangement 36 are activated, so that the electrodes 41a,b can alternatingly ignite and allow a spark to jump over to the mucosa 84. The argon shrouding forms a plasma beam 83a,b in front of each electrode 41a,b, this being shown by FIG. 5. The plasma beams 83a,b may combine to form a fan-shaped beam. The plasma beams 83a,b impinge chronologically offset next to each other on the mucosa 84 and coagulate its uppermost layer, in particular its epithelium 85, as well as the Lamina propria 86 and parts of the submucosa. However, the Muscularis propria 88 is preferably spared due to the previously formed fluid cushion.

Due to the alternating activation of the two plasma probes with 5 Hz, for example, there is a macroscopic combination of the plasma beams 83a,b. Thus, a wide tissue strip is coagulated with a uniform effective depth. Due to the angular arrangement of the ends 36a,b of the gas supply lines 35a,b and the electrodes 41a,b, the width of the tissue strip can be over 10 mm and, in the individual case, approximately 14 mm. The treatment is continued in that the user guides the instrument end 21 over the mucosa 84—by means of the control elements 14 of the endoscope 10 and by appropriately guiding the movement transmission element 25—along a path, in particular transversely to an imaginary line connecting the electrodes 41a,b to each other, at a distance from the tissue, in which case he/she leaves a strip of tissue having a width of approximately 12 mm to 20 mm. In this manner, it is possible to coagulate the mucosa 84 with great reliability and reduced danger of damaging the muscularis.

Figure 9:
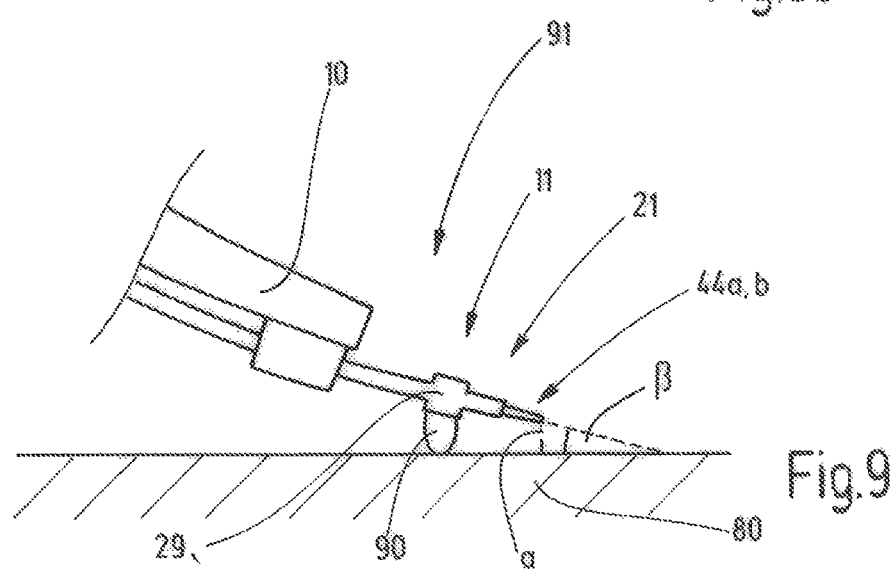

In order make maintaining a certain minimum distance between the distal ends of the plasma probes 44a,b and the tissue easier when guiding the instrument end 21 across the tissue within an angle greater than 0° and smaller than 90° (acute angle) between the longitudinal axis of the instrument end 21 and the tissue, the instrument 11 may comprise a sliding element 90 which is positioned attached to the instrument in such a manner that the instrument 11 rests on the tissue 80 via the sliding element 90. FIG. 9 shows, in a highly schematic manner, an exemplary embodiment of the system 91 according to the invention which comprises an instrument 11 that is configured, for example, in accordance with the description hereinabove and is held on an endoscope that, as indicated by a dashed line, is guided at an acute angle β over the tissue 80. The sliding element 90 of the instrument 11 can be attached, as illustrated, to the connecting element 29 or, for example, to the distal ends of the plasma probes 44a,b. Preferably, the sliding element 90 is arranged on the instrument 11 in such a manner that the instrument 11 preferably rests on the tissue 80 via the sliding element 90 in proximal direction in front of the treatment site. While the instrument 11 is being moved forward and backward, the sliding element 90 slides on the tissue, in which case—if a maximum angle β between the longitudinal axis of the distal instrument end 21 and the tissue 80 is not exceeded—the ends of the plasma probes 44a,b are guided at a certain minimum distance a, or—if a certain angle between the instrument end and the tissue is maintained, guided over the tissue at a certain distance a. Thus, the sliding element 90 promotes the homogeneity of the ablation. The angle β between the longitudinal axis of the distal instrument end 21 and the tissue while the instrument is being guided is preferable between more than 0° and 80°, particularly preferably a minimum of 20° and a maximum of 30°. The distance a or the minimum distance a (indicated in a dashed line in FIG. 9) between the distal ends of the plasma probes 44a,b, on the one hand, and the tissue 80, on the other hand, while the instrument end 21 is being guided over the tissue 80 with the sliding element 90 resting on the tissue 80 is preferably more than 0 mm up to preferably a maximum of 10 mm, particularly preferably more than 0 mm up to a maximum of 5 mm, for example more than 0 mm up to a maximum of 3 mm.

Figure 10A:
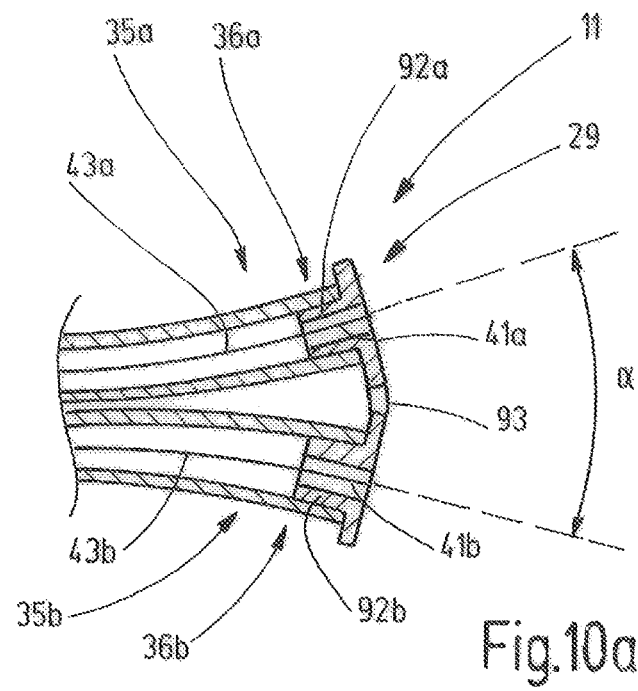
Figure 10B:
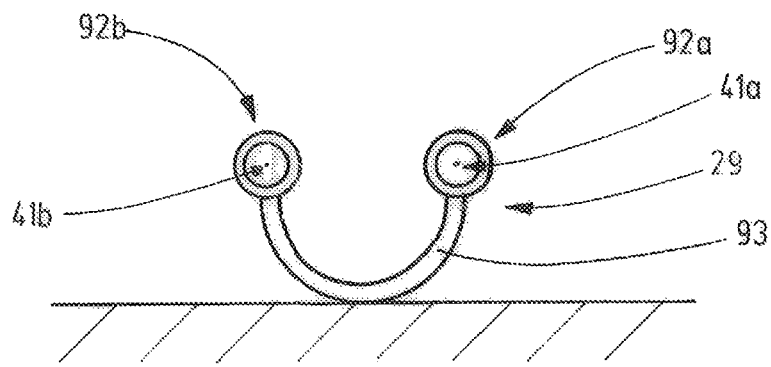

FIG. 10a shows an exemplary embodiment of the instrument 11 with a connecting element 29 that has two ceramic tube sections 92a,b that are inserted in the distal ends 36a,b of the gas supply lines 35a,b. The ceramic tube sections 92a,b are connected to each other by a connecting bracket 93 and oriented by the connecting bracket 93 at an acute angle α relative to each other, so that the ends 36a,b of the gas supply lines 35a,b are oriented at an acute angle α. The electrodes 41a,b and the electrical lines 43a,b are shown by a solid line inside the gas supply lines 35a,b. As shown by FIG. 10b, the bracket 93 extends in an arcuate manner transversely with respect to the longitudinal axis of the instrument 11 under the ceramic tube sections 92a,b. At the same time, the connecting bracket 93 acts as the sliding element 90 for the instrument 11.

Figure 10C:
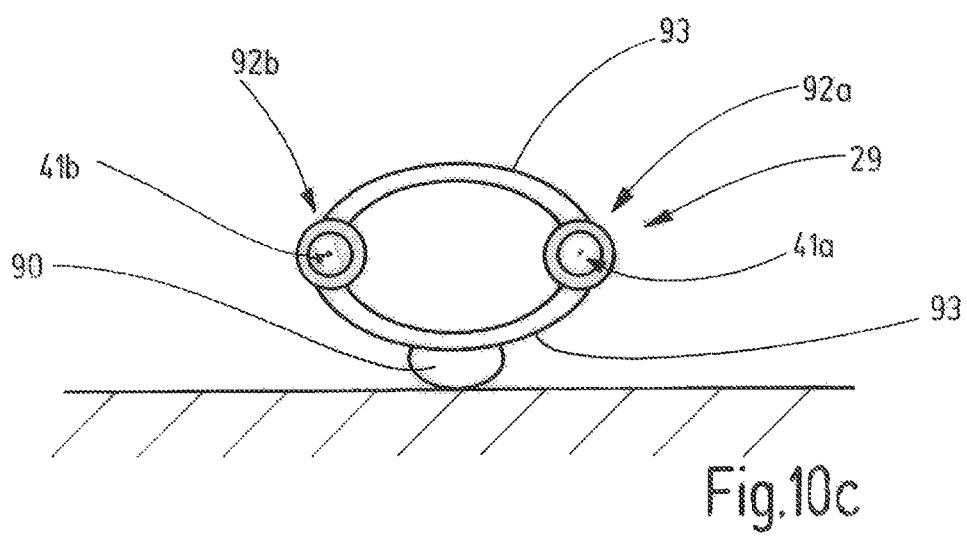

FIG. 10c shows a modification of the exemplary embodiment of the instrument 11 according to FIG. 10b with an additional connecting bracket 93 that connects the ceramic tube sections and extends in an arcuate manner transversely with respect to the longitudinal axis above the ceramic tube sections 92a,b. A sliding shoe 90 is arranged on at least one bracket 93, said sliding shoe acting as the sliding element.

The connecting element 29 of one of the embodiments described herein may be made in one part or multiple parts. For assembly of the instrument 11, the plasma probes 44a,b and/or the gas supply lines 35a,b may be inserted in the seats 51a,b, for example, in particular in the case of a one-piece connecting element 29, or set in or pressed in, e.g., in a half-shell of the connecting element 29. The connecting element 29 may be configured in such a manner that plasma probes 44a,b (individual probes) that can be used separately are respectively attached to a connecting element, in which case the connecting element components—if an instrument 11 according to the invention is needed—are attached to one another, and the individual probes 44a,b are thus arranged—relative to the instrument 11—at an angle α and the free space 45 between the distal ends of the plasma probes 44a,b.

According to the invention an instrument 11 is provided, which instrument can be used, in particular, for the large-area ablation of tissue, in an example for the ablation of the mucosa 84, in which case the instrument 11 comprises at least one first gas supply line 35a and at least one second gas supply line 35b, whose distal ends 36a,b are arranged in such a manner that they form an acute angle α, so that the ends 36a,b of the gas supply lines 35a,b diverge distally in order to produce distally diverging gas flows in the distal ends 36a,b of the gas supply lines 35a,b when the gas supply lines 35a,b are charged with gas. Between the distal ends 36a,b of the gas supply lines 35a,b, there is provided a free space 45 that allows the user of the instrument 11 to look through the free space 45 between the distal ends 36a,b of the gas supply lines 35a,b through to the tissue region 47 behind the distal end 21 of the instrument 11. The free space 45 is preferably open in distal direction. Due to the acute angle α, it is possible, by means of electrodes 41a,b arranged at least partially in the ends 36a,b of the gas supply lines 35a,b, to generate a wide plasma beam with which the mucosa ablation can be performed. In doing so, the instrument 11 can be guided particularly precisely due to the view through the free space 45. A connecting element 29 according to the invention is provided for attaching the ends 36a,b of the gas supply lines 35a,b. The connecting element 29 may have, on its distal end 31, separate extensions 53a,b, in which case the gas supply lines 35a,b extend through said extensions. Alternatively or additionally, the distal ends 36a,b of the gas supply lines 36a,b are preferably arranged separately extending away from the connecting element 29.

REFERENCE SIGNS

| 10 | Endoscope |
|---|---|
| 11 | Instrument |
| 12 | Stomach |
| 13 | Esophagus |
| 14 | Control elements |
| 15 | Distal end of the endoscope |
| 16 | Channels |
| 18 | Tubular sleeve |
| 19a, b | First lumen, second lumen |
| 20 | Sheathing tube |
| 21 | Distal instrument end/instrument head |
| 22 | Axial direction |
| 23 | Longitudinal axis of the instrument end |
| 24 | Socket |
| 25 | Movement transmission element |
| 27a, b | Gas supply line tubes |
| 28 | Fluid supply line |
| 29 | Connecting element |
| 30 | Proximal end of the connecting element |
| 31 | Distal end of the connecting element |
| 32 | Anti-twist device |
| 33 | Shaped catch, spring |
| 34 | Groove, slit |
| 35a, b | First, second gas supply lines |
| 36a, b | Ends of the gas supply line |
| 37a, b | Center axes |
| 38a, b | Plastic line |
| 39a, b | Ceramic tube |
| 40a, b | Distal ends of the plastic lines |
| 41a, b | First, second electrodes |
| 43a, b | Electrical lines |
| 44a, b | Plasma probes |
| 45 | Free space |
| 46a, b | Proximal ends of the ceramic tube |
| 47 | Tissue region |
| 51a, b | Seats |
| 53a, b | Extensions |
| 56a, b | Sections of the gas supply lines |
| 60 | Head of an additional probe |
| 61 | Additional probe/fluid jet probe |
| 62 | Double arrow |
| 65 | Seat for the additional probe |
| 66 | Center axis of the additional probe |
| 68 | Arrow |
| 69 | Arrow |
| 75 | Switch arrangement |
| 76 | Source |
| 77 | High-frequency generator |
| 78 | Neutral electrode |
| 80 | Tissue region |
| 81 | Tissue site |
| 82 | Stomach wall |
| 83a, b | Plasma beam |
| 84 | Mucosa |
| 85 | Epithelium |
| 86 | Lamina propria |

-continued

| 87 | Submucosa |
|---|---|
| 88 | Muscularis propria |
| 90 | Sliding element/sliding shoe |
| 91 | System |
| 92a, b | Ceramic tube sections |
| 93 | Connecting bracket |
| 94 | Image |
| α | Acute angle |
| β | Angle |
| a | Distance |

The invention claimed is:

1. An instrument for treatment of a tissue, comprising:
a first gas supply line with a first electrode that is arranged at least partially in said first gas supply line, and
a second gas supply line with a second electrode that is arranged at least partially in said second gas supply line,
wherein the first gas supply line and the second gas supply line are arranged relative to each other in such a manner that a distal end of the first gas supply line forms an acute angle (α) with a distal end of the second gas supply line, so that the first gas supply line and the second gas supply line diverge in a distal direction at their distal ends,
wherein, a free space is provided between the distal end of the first gas supply line and the distal end of the second gas supply line, wherein the free space is configured to allow a user to view between the distal ends of the first and second gas supply lines through to a region of effect of the instrument in front of the distal ends of the gas supply lines.

2. The instrument according to claim 1, wherein the first gas supply line and the first electrode are associated with a first probe and the second gas supply line and the second electrode are associated with a second probe, wherein the first probe and the second probe are held by a connecting element in such a manner that the distal end of the first gas supply line forms the acute angle (α) with the distal end of the second gas supply line.

3. The instrument according to claim 2, wherein at least one of the first and second probes is configured to interchangeably attach with the connecting element.

4. The instrument according to claim 2, wherein the distal ends of the first and second gas supply lines project distally beyond the connecting element.

5. The instrument according to claim 2, wherein at least one section of the first gas supply line is configured as a first plastic line that extends, without interruption, through the connecting element, and wherein at least one section of the second gas supply line is configured as a second plastic line that extends, without interruption, through the connecting element.

6. The instrument according to claim 1, wherein the first gas supply line comprises a first ceramic tube that is inserted in a distal end of a first plastic line of the first gas supply line, and wherein the second gas supply line comprises a second ceramic tube that is inserted in a distal end of a second plastic line of the second gas supply line.

7. The instrument according to claim 6, wherein the first gas supply line and the first electrode are associated with a first probe and the second gas supply line and the second electrode are associated with a second probe, wherein the first probe and the second probe are held by means of a connecting element, and wherein proximal ends of the first and second ceramic tubes are arranged in the connecting element.

8. The instrument according to claim 6, wherein the first and second ceramic tubes project, at the distal ends of the gas supply lines, distally beyond the first and second plastic lines.

9. The instrument according to claim 1, wherein the instrument comprises an additional probe having a distal end arranged on a distal end of the instrument.

10. The instrument according to claim 9, wherein the first gas supply line and the first electrode are associated with a first probe and the second gas supply line and the second electrode are associated with a second probe, wherein the first probe and the second probe are held by means of a connecting element, and wherein the additional probe is arranged in a seat of the connecting element for the additional probe.

11. The instrument according to claim 9, wherein the additional probe is configured to move, relative to an arrangement of the distal end of the first gas supply line and the distal end of the second gas supply line, in a proximal direction out of the free space.

12. The instrument according to claim 1, further comprising a sliding element for guiding the instrument over the tissue.

13. The instrument according to claim 2, wherein the connecting element has a first and second distal extension, wherein the first gas supply line extends through the first extension and the second gas supply line extends through the second extension, and wherein the free space extends between the distal extensions.

14. A system comprising an endoscope and an instrument for treatment of a tissue, wherein the instrument is fastened to an outside of the endoscope, the instrument comprising:
    a first gas supply line with a first electrode that is arranged at least partially in said first gas supply line, and
    a second gas supply line with a second electrode that is arranged at least partially in said second gas supply line,
    wherein the first gas supply line and the second gas supply line are arranged relative to each other in such a manner that a distal end of the first gas supply line forms an acute angle (a) with a distal end of the second gas supply line, so that the first gas supply line and the second gas supply line diverge in a distal direction at their distal ends,
    wherein, a free space is provided between the distal end of the first gas supply line and the distal end of the second gas supply line, wherein the free space is configured to allow a user to view between the distal ends of the first and second gas supply lines through to a region of effect of the instrument in front of the distal ends of the gas supply lines.

15. A method for tissue ablation with an instrument comprising:
    a first gas supply line with a first electrode that is arranged at least partially in said first gas supply line, and
    a second gas supply line with a second electrode that is arranged at least partially in said second gas supply line,
    wherein the first gas supply line and the second gas supply line are arranged relative to each other in such a manner that a distal end of the first gas supply line forms an acute angle with a distal end of the second gas supply line, so that the first gas supply and the second gas supply line diverge in a distal direction at their distal ends,
    wherein a free space is provided between the distal end of the first gas supply line and the distal end of the second gas supply line, wherein the free space is configured to allow a user to view between the distal ends of the first and second gas supply lines through to a region of effect of the instrument in front of the distal ends of the gas supply lines;
    the method comprising:
    moving the instrument along a path, transversely with respect to a line connecting the first and second electrodes, at a distance from tissue to be ablated.

16. The method according to claim 15, further comprising applying a radiofrequency (RF) voltage to the first and second electrodes and alternatingly pulsing the RF voltage between the first and second electrodes.

17. The method according to claim 15, further comprising, before thermal ablation of a mucosa by the instrument, introducing fluid into a stomach wall in such a manner that a fluid cushion will form under a desired ablation site.

18. The instrument according to claim 9, wherein the additional probe is configured to be slid in the distal direction beyond the distal ends of the first and second gas supply lines.

* * * * *